United States Patent [19]

Swaine

[11] 4,215,799

[45] Aug. 5, 1980

[54] DISC DISPENSER

[75] Inventor: Derwent Swaine, Winchester, England

[73] Assignee: Oxoid Limited, Hampshire, England

[21] Appl. No.: 925,954

[22] Filed: Jul. 18, 1978

[30] Foreign Application Priority Data

Jul. 22, 1977 [GB] United Kingdom ............... 30934/77

[51] Int. Cl.$^2$ ........................ B65H 3/44; B65G 59/06
[52] U.S. Cl. .................................... 221/93; 221/211; 221/236; 221/252; 221/197; 221/132
[58] Field of Search ............... 221/211, 236, 252, 268, 221/272, 273, 197, 93, 132

[56] References Cited

U.S. PATENT DOCUMENTS

| 3,144,168 | 8/1964 | Campbell et al. | 221/211 X |
| 3,152,700 | 10/1964 | Poulin | 221/211 X |

*Primary Examiner*—Allen N. Knowles
*Attorney, Agent, or Firm*—Wenderoth, Lind & Ponack

[57] ABSTRACT

A dispenser for antibiotic sensitivity discs which automatically and simultaneously dispenses a plurality of discs onto a flat surface, for example a layer of agar gel in a petri dish. The dispenser comprises a removable magazine unit which carries the required number of standard cartridges, each filled with discs to be dispensed. The discs are in turn removed mechanically from the cartridges from where they are transferred to the surface of the gel by a plurality of pick-up tubes to which a vacuum is applied. The vacuum causes the discs to become attached to the ends of respective tubes so that the discs move with the tubes onto the gel surface, and are pressed onto the gel surface by a pressure equal to the weight of the tubes.

15 Claims, 11 Drawing Figures

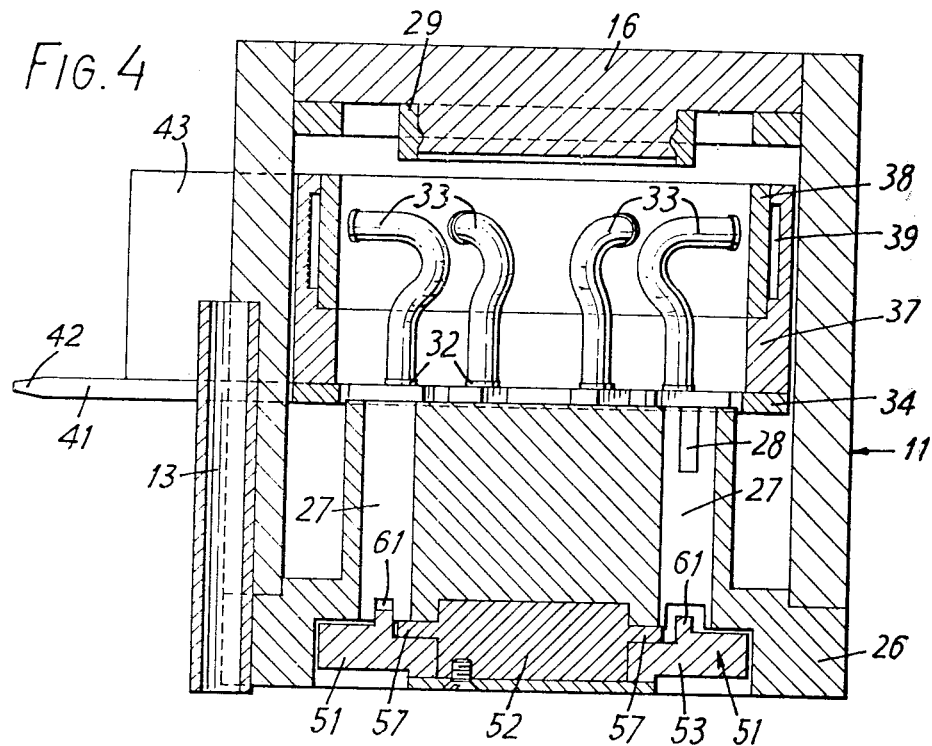
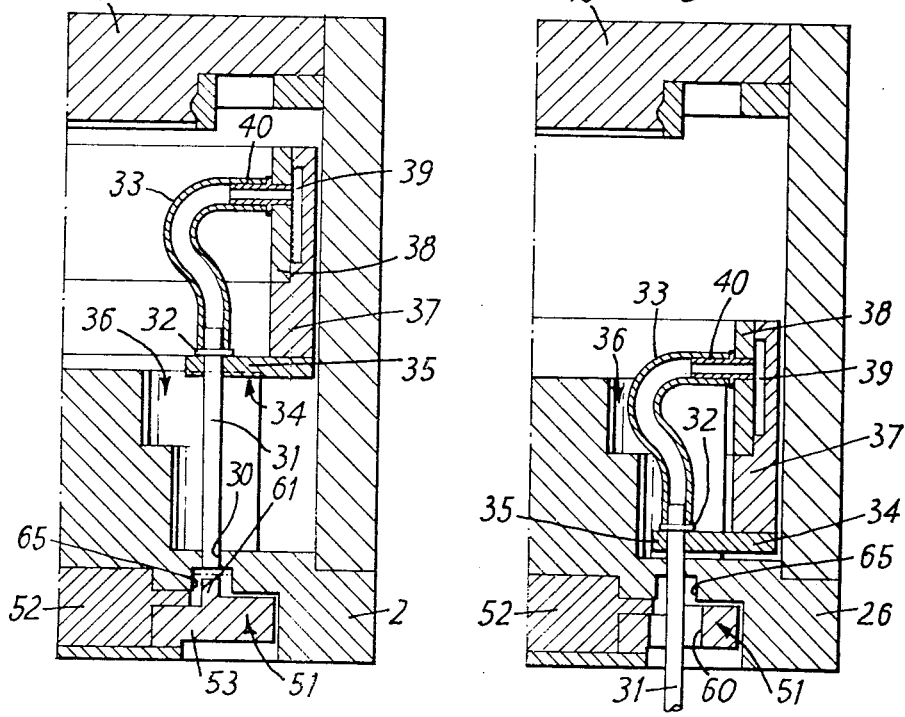

DISC DISPENSER

BACKGROUND OF THE INVENTION

This invention relates to a method of dispensing discs or other flat objects and to a dispenser for carrying out such method. The invention is particularly, although not exclusively, concerned with a dispenser for the simultaneous transfer of a plurality of sensitivity discs, each impregnated with a different substance, for example various antibiotics, onto a flat surface formed by a thin layer of agar gel in a petri dish or similar container.

Such dispensers may be used in antibiotic susceptibility testing, the agar gel acting as a sterile nutrient medium for the organism being analysed. The organism is introduced onto the surface of the gel, and the discs are distributed over the surface of the gel by means of the dispenser. Each disc contains a different antibiotic, so that the effect on the organism of a plurality of different antibiotics can be simultaneously studied. The use of impregnated discs in this way is well known and will not be described further.

Several dispensers for the simultaneous dispensing of a plurality of discs are already known. The discs are generally stacked one on top of another in an elongate cylindrical cartridge. The discs are biassed to an exit end of the cartridge by means of an internal coil spring. Any one cartridge contains only discs impregnated with one particular antibiotic, details of which are displayed on the exterior of the cartridge.

Small hand dispensers can be made quite cheaply but generally suffer from the disadvantage that the positioning of the discs on the agar gel is not sufficiently precise for many purposes. The reason for this is that, in order to avoid undue force in applying each disc to the surface of the gel, most dispensers allow the discs to drop freely under gravity for a short distance onto the gel surface, this gravitational fall thus forming the final part of the transfer of the discs from their respective cartridges to the surface of the gel.

Other dispensers meet stringent disc positioning requirements, but fail because they apply the discs to the surface of the gel either with too much force, thus damaging the gel surface and burying the disc in the surface, or with differing forces as between different discs—some discs being pressed harder into the gel than others—and this immediately leads to non-comparable results as between the discs.

SUMMARY OF THE INVENTION

The present invention seeks to provide a disc dispenser which is capable of high positional accuracy of disc placement together with a very small and substantially constant force applied to the discs as they are applied to the gel surface. The dispenser also has the advantage that it can be made almost completely automatic for rapid analysis of clinical samples, thus facilitating its use in situations such as hospitals and laboratories where a considerable number of tests must be made.

In accordance with a first aspect of the invention there is provided a method of dispensing flat objects, which objects are placed in a stack for dispensing, said method comprising the steps of moving one object from the end of the stack to a pick-up position, applying suction to a transfer pipe to thereby hold said one object on the free end of the pipe, moving the pipe so that the object is transferred with the pipe from the pick-up position to a releasing position, and terminating the suction applied to the pipe to thereby release the object.

While the above method is described in relation to the dispensing of one object at a time, it will be clear that the method can easily be adapted to cope simultaneously with a plurality of individual stacks of flat objects, a different transfer pipe being used for each respective stack. For convenience, all such different transfer pipes may be connected to a common vacuum source for simultaneous application and termination of vacuum.

In accordance with a second aspect of the invention there is provided a dispenser for flat objects, which objects are placed in a stack for dispensing, said dispenser comprising means for moving one object from the end of the stack to a pick-up position, a transfer pipe to which suction may be applied in order to hold said one object onto one end of the pipe, means for moving said pipe from a first position in which it can pick up the object by suction to a second, releasing, position and means for terminating the suction applied to the pipe when it reaches the releasing position to thereby release the object.

Preferably all the operations are carried out automatically by means of a simple mechanical or electronic control means.

One important requirement for antibiotic disc dispensers, as described above, is for a uniform and small pressure to be applied to the discs as they are applied to the gel. In a preferred embodiment of the present invention, this requirement is met by applying the suction to a small low-weight transfer pipe which moves vertically in a direction along its own axis to move the disc being dispensed from the pick-up position to the releasing position (i.e. the gel surface). It is arranged that when the pipe and its disc reaches the gel surface, the pipe rests by its own weight only on the gel surface, thus applying a small pressure on the disc, sufficient to ensure contact with the gel surface, but not great enough to force the disc into the gel surface. In a dispenser for the simultaneous dispensing of a plurality of discs, even pressure between discs can be achieved by using a similar transfer pipe for each disc to be dispensed, thus ensuring that each disc is applied to the gel surface with substantially the same pressure.

DESCRIPTION OF THE DRAWINGS

In order that the invention may be better understood, an emmbodiment thereof will now be described by way of example only and with reference to the accompanying drawings in which:

FIG. 4 is a sectional view along the lines IV—IV of FIG. 3;

FIGS. 5A and 5B are section views along the lines V—V of FIG. 3 showing two different positions of the magazine unit;

DETAILED DESCRIPTION OF THE PREFERRED EMBODIMENTS

Figure 1:
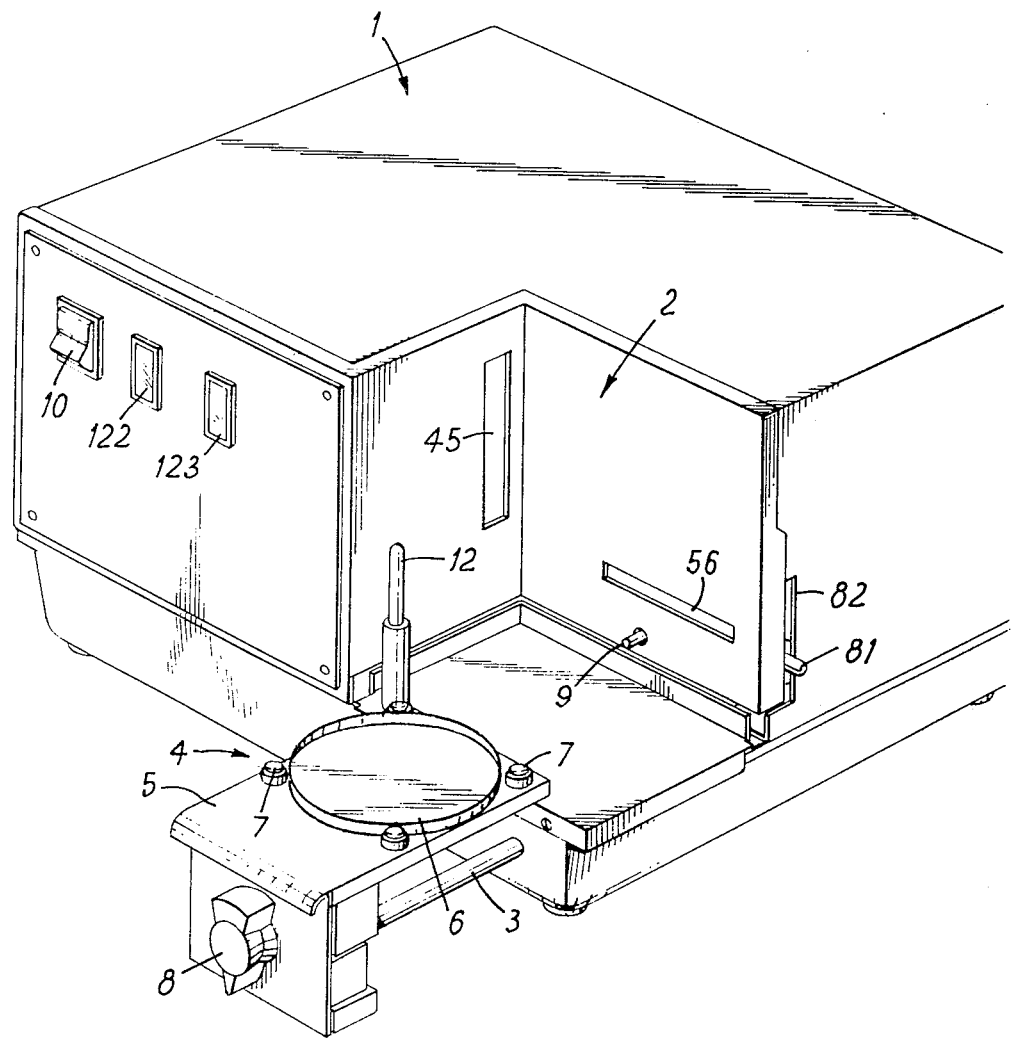
FIG. 1 is a general perspective view of an automatic disc dispenser according to the invention.

Referring to FIG. 1, the dispenser comprises a substantially rectangular housing 1 having a rectangular recess 2 in one corner. The front wall of housing 1 is formed with a pair of apertures through which slide respective round bars 3 which support a movable carriage 4. The carriage 4 has a horizontal surface 5 for supporting a removeable petri dish 6. Upstanding pegs 7 securely locate the dish 6 on surface 5. Vertical adjustment of the surface 5, and hence dish 6 is provided by means of a knob 8.

The petri dish 6 is intended to contain a thin layer of nutrient agar gel (not shown) onto or into which an organism under test has previously been seeded or otherwise applied, using known techniques. The purpose of the dispenser is to deposit onto the surface of this layer of agar gel an array of evenly spaced sensitivity discs, each disc containing a different antibiotic. Once the discs have been deposited, the petri dish and its contents are removed so that the effect of each antibiotic on the organism can be assessed. The number of discs deposited by the dispenser described herein is eight, evenly distributed around a circle. It will be understood, however, that different numbers of discs and different patterns of discs can easily be accommodated by this dispenser, as will become clear hereinafter.

,The carriage 4 is moveable between a first position (as illustrated) in which the petri dish may be placed on and removed from the surface 5 and a second position (not shown) in which the carriage surface 5 is directly above the floor of the recess 2. In this second position, the side wall of the petri dish which protrudes from the carriage 4 is arranged to depress a microswitch operating button 9 in order to initiate the sequence of events which eventually leads to the dispensing of the discs onto the gel surface. A main on-off switch 10 controls the main supply of power to the dispenser.

The housing 1 contains the components necessary for the operation of the magazine unit, shown in detail under reference 11 in FIGS. 2 to 8, and these components will be described in more detail as they appear in the following text.

During operation of the dispenser, the magazine unit 11 must first be fitted into the recess 2 of the housing 1 and, to this end, there is fitted on the floor of the recess 2 a vertical post 12. The post 12 fits into an aperture 13 provided in the magazine unit so that the magazine unit can be swung into position about the post 12. The post 12 has an enlarged lower end which defines a shoulder on which the magazine unit rests. The correct vertical position of the magazine unit is thus assured.

In order to use the dispenser, the magazine unit is thus fitted over the post 12 and swung in an anticlockwise direction until it locks into position, as will be explained hereinafter. In its operational position, the magazine unit is conveniently of substantially the same size as the recess 2, so that the magazine unit roughly fills in that corner of the housing 1. The presence of the shoulder on post 12 ensures that a space is left between the bottom of the magazine unit, when fitted, and the floor of recess 2 so that the carriage 4 and petri dish 6 may be moved into position beneath the magazine unit.

Figure 2:
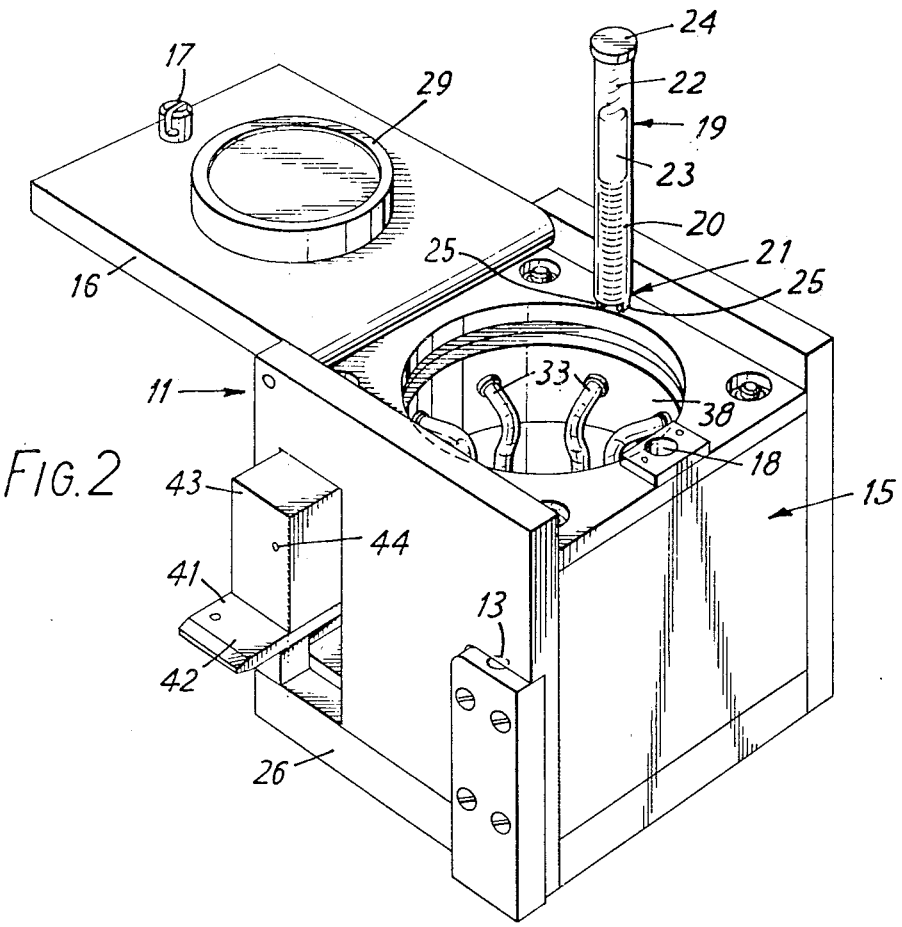
FIG. 2 is a perspective view of a removable magazine unit which forms part of the dispenser of FIG. 1.
Figure 3:
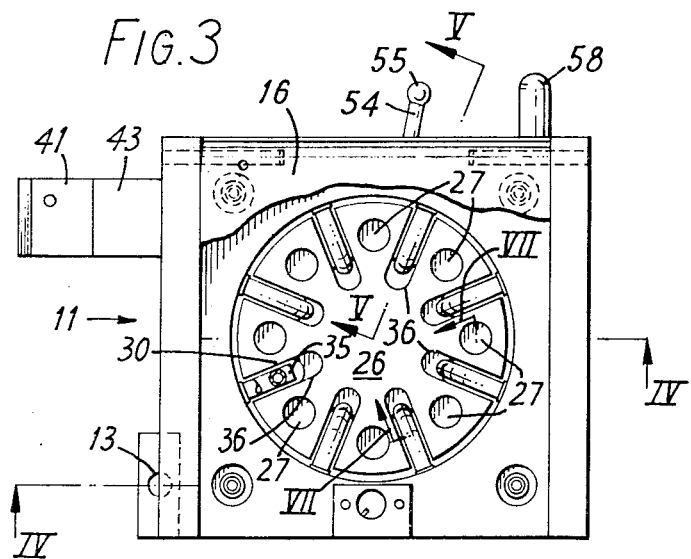
FIG. 3 is a plan view of the magazine unit of FIG. 2 with part of the cover removed.

It will be seen from FIG. 2 that the magazine unit 11 comprises a substantially rectangular box 15 having a hinged lid 16. The box 15, including lid 16, are preferably made from transparent material, for example plastic material, so that operation of the unit can be monitored visually. The lid 16 is secured when in the closed position by means of a bayonet locking screw 17 which cooperates with a fastening device 18 at the top of the front wall of the box 15. A peg 58 is rigidly attached to the rear wall of the box 15 and serves to lock the magazine unit in its operational position, as will be explained hereinafter.

The antibiotic discs to be dispensed are contained in eight individual cylindrical cartridges 19. The discs are piled on top of one another in a stack 20 within each cartridge and are biassed towards one end 21 of the cartridge by means of a coil spring 22 and plunger 23. A cap 24 closes the other end of the cartridge. The end 21 of the cartridge which, in use, is the lower end, is open, but is equipped with a pair of downwardly extending lugs 25 which extend slightly into the path of the discs to prevent movement of the bottom disc of the stack in a direction along the axis of the cartridge. However the lugs 25 are so positioned and shaped as to allow one disc at a time to be slid off the stack in a direction at right angles to the axis of the cartridge. The geometry is such that only movement in one direction is possible.

The housing 16 is closed at the lower end by a bottom member 26 which has a plurality of apertures arranged around a circle. There are sixteen such apertures in all, arranged in two groups of eight. The first group of apertures, each referenced 27, are of larger diameter than the others, and each take the form of a circular bore into which a respective cartridge 19 may be fitted.

The upper end of each cartridge locating bore has a slot 28 which cooperates with a protrusion (not shown) on the cartridge 19, in order to ensure correct orientation of the cartridge, when fitted. The cartridges are retained in their correct positions by means of a ring 29 of resilient material fixed to the inside face of the lid 16. During normal operation of the dispenser, all eight cartridge locating tubes will be fitted with a respective cartridge containing discs to be dispensed and, with this arrangement, eight discs will be simultaneously dispensed on each cycle of operation. However, it is possible to omit some cartridges if fewer than eight are sufficient.

The remaining group of eight apertures, each referenced 30, in the bottom member 26 are intended each to receive a respective stainless steel transfer pipe 31. The transfer pipes 31, of which there are eight, are slidingly received in their respective apertures 30, and so are capable of vertical movement, as shown by the arrows in FIG. 7.

Each transfer pipe 31 has a small flange 32 fixed close to its upper end. That part of pipe 31 above the flange is attached to a short length 33 of flexible tube, for example of plastic material. In the normal position, shown in FIGS. 4 and 5, the flange 32 rests on a flat, generally circular, support plate 34. The support plate 34 is generally annular in shape, and is equipped with eight radially inwardly extending wings 34, evenly spaced apart. Each wing has a respective aperture in register with and of the same size as a corresponding aperture 30 in the bottom member 26. The transfer pipes 31 are thus fit slidingly in these apertures also. Each wing 35 extends into a corresponding radially inwardly extending slot 36 in the bottom member 26. The plate 34 is thereby restrained against rotation, but is able to slide up and down with respect to the member 26.

Upstanding from the perimeter of plate 34, and attached thereto, is a short tubular distribution member 37. The member 37 has an inner sleeve 38 affixed thereto, the member 37 being shaped such that the sleeve, when fitted, defines an annular rectangular section passageway 39. Extending radially inwardly from the sleeve 38 are eight evenly spaced lengths 40 of pipe which each communicate with the passageway 39, as shown most clearly in FIG. 5. The opposite end of each length 33 of flexible tube is fitted over a respective length 40 of pipe.

The plate 34 has an outwardly extending tangential protrusion 41 which is tapered at its end 42. The distribution member 37 is similarly provided with a shorter tangential protrusion 43. The protrusion 43 carries an air passageway from the passageway 39 to an orifice 44 at the outer surface of the protrusion 43. When the magazine unit is swung into position about the post 12, the protrusions 41 and 43 enter a rectangular cutout 45 in the housing 1 for reasons which will be explained hereinafter.

The protrusions 41 and 43 are movable in a vertical direction within cut-out 45 by means (not shown in FIGS. 1 to 8) within housing 1. During this movement the protrusions remain horizontal and carry with them the distribution member 37 and support plate 34. The position shown in FIGS. 4 and 5A is the uppermost position of the plate 34. As the plate is moved downwards, the transfer pipes 31 also move downwards until the bottom of the transfer pipes meet the surface of the gel in the petri dish 6. This position is shown in FIG. 5B. Any further downwards movement of the plate 34 causes the transfer pipes to slide in the apertures provided for them in the plate 34, thus lifting the flanges 32 above the plate 34. Upwards return movement of the plate 34 causes the flanges 32 to re-engage the plate 34 so that the transfer tubes 31 are lifted back to the position shown in FIG. 5A.

A circular flat transfer plate 51, made of plastic material, is rotatably mounted against the undersurface of the bottom member 26. The plate 51 is made in two parts: a central part 52 which bears against the member 26; an outer annular part 53 carrying apertures and ridges, to be referred to later. The transfer plate 51 is biased to its extreme anticlockwise position (when viewed from above) by means of a spring (not shown). The central part 52 is equipped with an outwardly extending rim 57 which protrudes slightly into the bores 27. The rim 57 is arranged so as not to affect the dispensing operation, but to protrude sufficiently to act as a stop in order to define the vertical position of the cartridges. The cartridges are thus inserted into the respective bores 27 and are pressed down until the lugs 25 bear against the rim 57. The lid 16 is then closed, whereupon the resilient ring 29 bears against the top of the cartridges and retains them firmly in position.

Rotational movement of the transfer plate 51 is effected by means of a lever 54 having an enlarged end 55, which lever is attached to the transfer plate and extends through an elongated recess (not shown) in the bottom member 26. When the magazine unit is swung into position about the post 12, the lever 54 and peg 58 enter a cut-out 56 in the housing 1 and engage a locking lever assembly, described in detail hereinafter.

Figure 6:
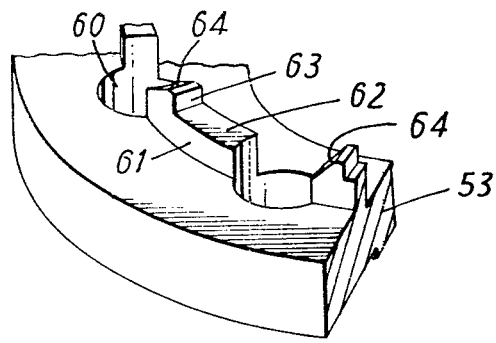
FIG. 6 is an enlarged view of part of the upper surface of the transfer plate which forms part of the magazine unit of FIG. 2.
Figure 7:
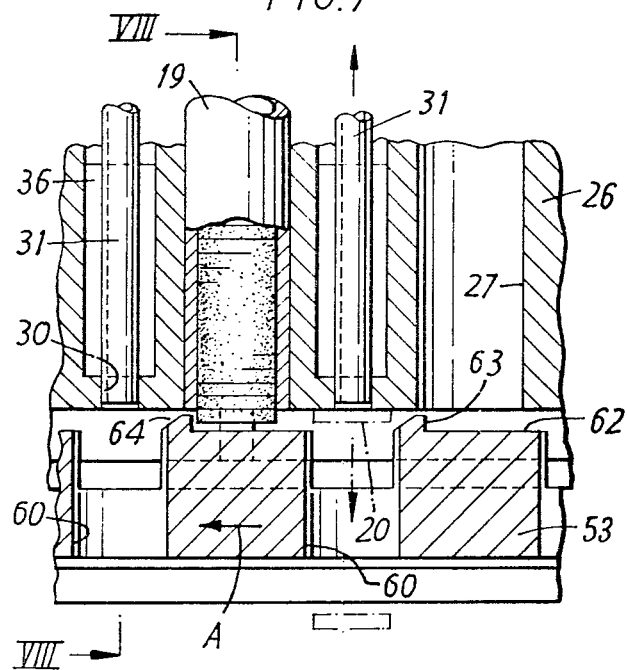
FIG. 7 is a curved section along the lines VII—VII of FIG. 3 of part of the lower portion of the magazine unit, showing the interaction between the transfer plate, transfer tube and cartridges.
Figure 8:
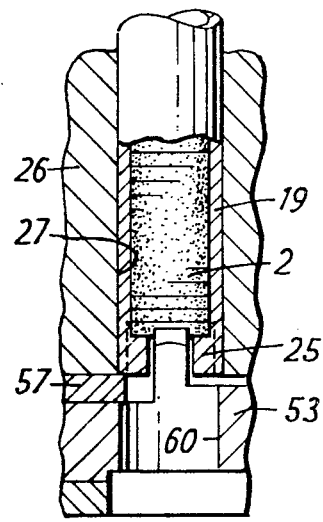
FIG. 8 is a sectional view along the lines VIII—VIII of FIG. 7.

The upper surface of the part 53 of the transfer plate 51 is shaped as shown in the enlarged views of FIGS. 6, 7 and 8. The plate is equipped with eight equally spaced apertures 60 arranged in a circle coaxial with the plate itself. These apertures are such that they are approximately the same size as the discs to be dispensed, but sufficiently large to enable the disc to pass easily therethrough. In the normal, fully clockwise, position of the plate 51, each of the apertures 60 is in register with a respective aperture 27 in the bottom member 26. The plate 51 moves between this position and one in which each aperture 60 is in register with a respective aperture 30—this latter position is shown in FIG. 7. The total rotary movement of plate 51 is the pitch between adjacent apertures 27 and 30.

In between each aperture 60 is formed, on the upper surface of plate 51, an upstanding ridge 61. There are thus eight of these upstanding ridges, all identical in shape to that shown in FIG. 6. The top surface of each ridge 61 comprises a flat portion 62, parallel to the upper surface of the plate, followed by an upstanding shoulder 63 and a sloping portion 64. The upstanding ridges 61 move within the confines of a circular slot 65 cut in the under surface of the bottom member 26.

Figure 9:
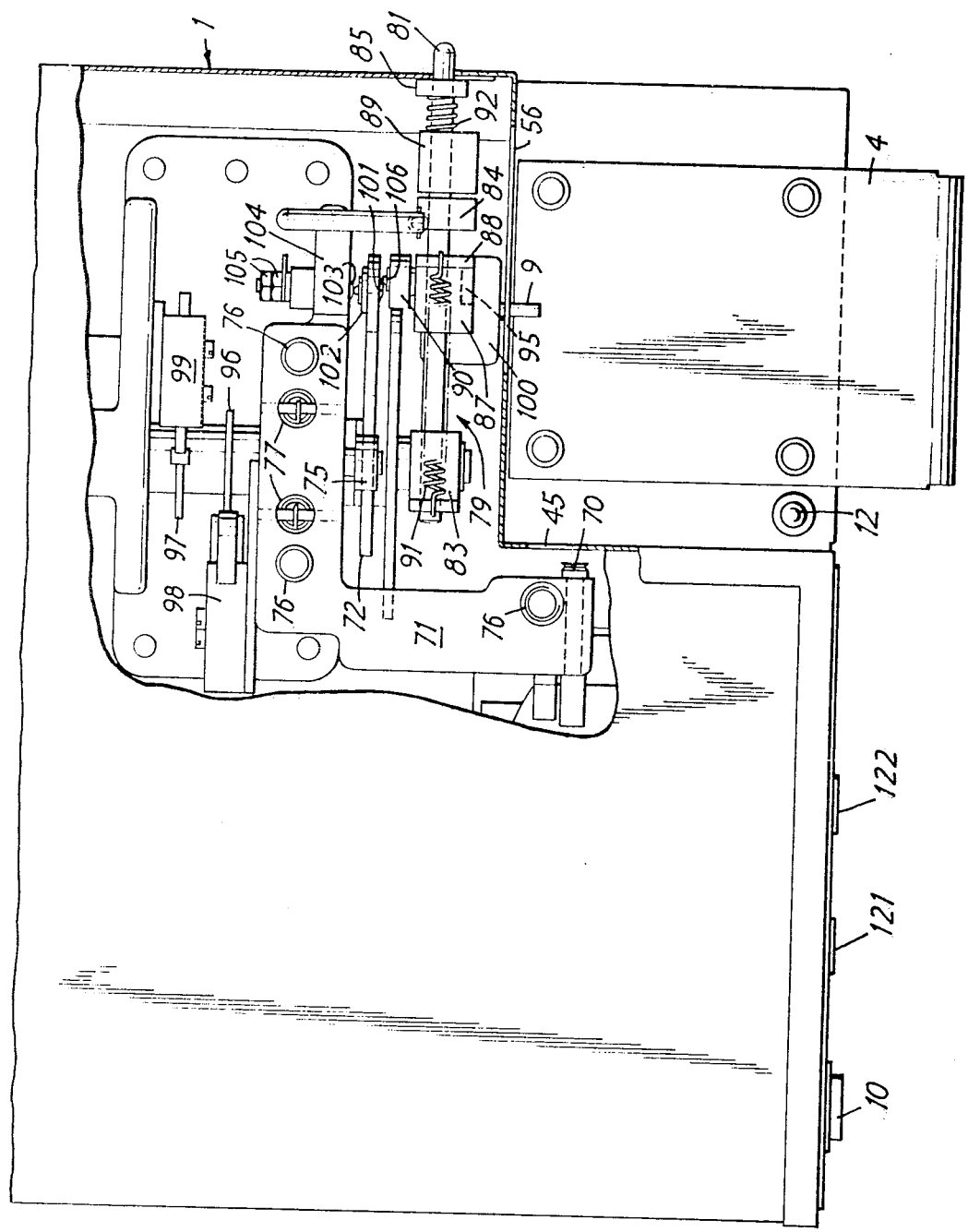
FIGS. 9 and 10 are plan and front view respectively of the disc dispenser in which part of the cover is cut away to show internal details.

Particular reference will now be made to FIGS. 9 and 10 which show how the mechanical and hydraulic requirements of the magazine unit 11 are met.

When the magazine unit is swung into position, the orifice 44 in the protrusion 43 comes into contact with an orifice 70 on a cam follower block 71. By this means vacuum is applied, via the orifices 44 and 70 to the transfer pipes 31 in the magazine unit. The manner in which this is achieved is described in more detail in relation to FIG. 11.

Vertical movement of the support plate 34 and rotational movement of the transfer plate 51 are effected by cams 72 and 73 respectively, both mounted for simultaneous rotation on a shaft 74. The shaft 74 is rotated by an electric motor via drive belts (both not shown).

The cam 72 acts on a cam follower 75 rotatably mounted on the cam follower block 71. The block 71 is mounted for vertical movement only on three vertical shafts 76, mounted rigidly on the housing 1. A pair of vertical coil springs 77, positioned in respective bores machined in the block 71 act to bias the block 71 in a downwards direction, thus biasing the cam follower 75 against the cam 72.

When the magazine unit is swung into position, the protrusion 41 extends into a corresponding slit 78 in the cam follower block 71. As the cam 72 rotates, the cam follower block 71, and hence the support plate 34 in the magazine unit moves vertically and, provided the cam profile is correct, the sequence of movement described previously will be executed.

The motion of the cam 73 is transferred to the lever 54 in the magazine unit 11 via the agency of a locking lever assembly 79. The assembly 79 comprises a pair of parallel metal rods 80 and 81, of which rod 81 protrudes through an elongate cut-out 82 in the housing 1. Three link members 83, 84 and 85 are attached to the rods 80, 81 and fixedly link the rods together in the manner of the sleepers of a railway track. The link member 83 is freely mounted for rotation about the shaft 74 and the whole assembly 79 is biased in an anticlockwise direction by means of a coil spring 86 attached to the link member 84.

Three further link members 87, 88 and 89 are movably mounted on the rods 80 and 81. The link member 87 carries a cam follower 90 which acts against the cam 73. A pair of coil springs 91 act between the fixed link member 83 and the movable link member 88 and act to urge the link member 88 towards shaft 74, thus causing the the member 88 to be urged against the link member 87 and hence the cam follower 90 to be biased against the cam 73. The movable link member 89 is biased against the fixed link member 84 by means of a pair of coil springs 92.

Figure 10:
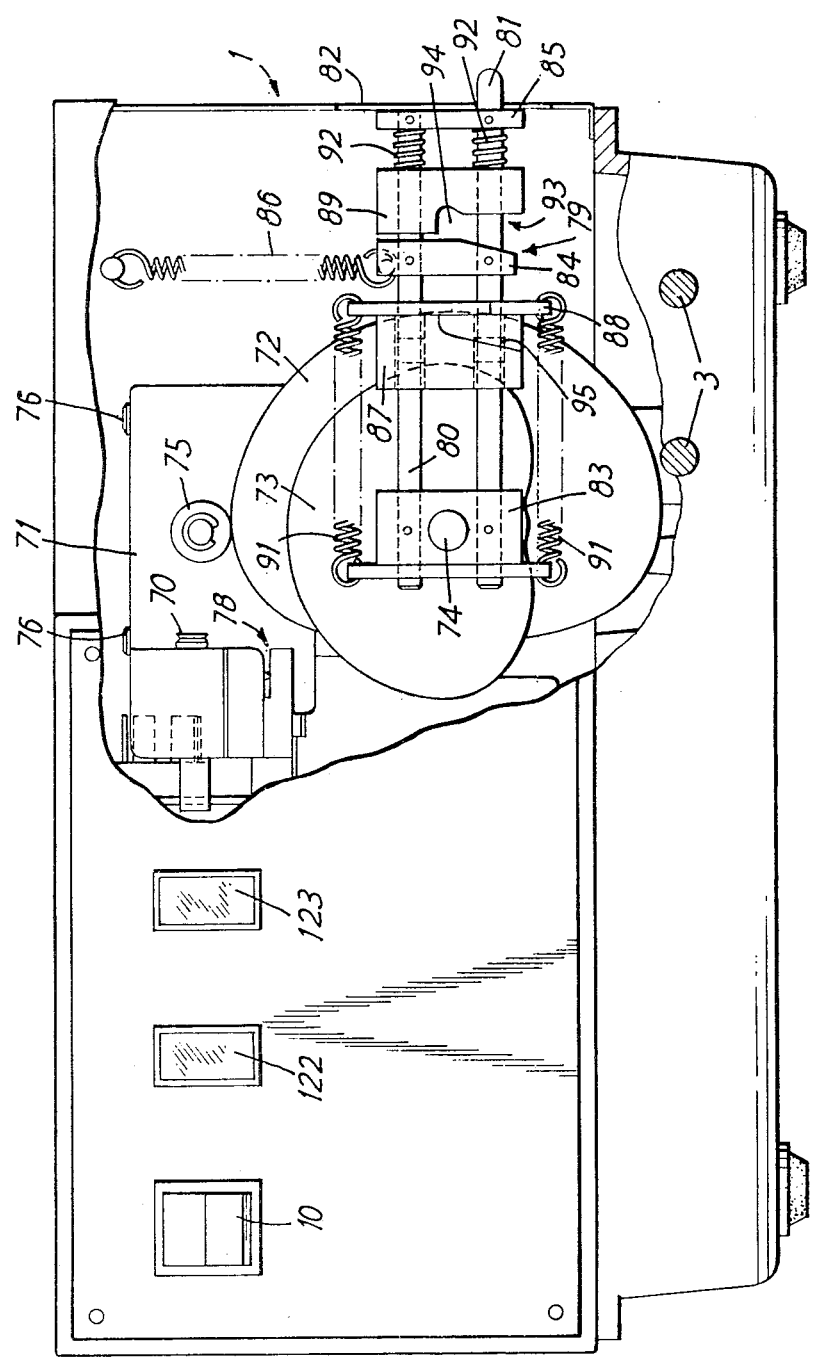

In its normal position, the lever arrangement 79 is biased about 20° anticlockwise from the position illustrated in FIG. 10. In this latter position the arrangement 79 lies above the cut-out 56 in the housing 1. In order to lock the magazine unit in position the unit is swung about the post 12 so that the peg 58 enters the cut-out 56. The protruding part of rod 81 is thence pressed downwards by hand, thus causing the lever assembly 79 to rotate clockwise to the position shown in FIG. 10. In so doing the peg 58 enters the tapering gap 93 formed between the fixed link member 84 and the moving link member 89, thus causing rightwards movement of the link member 89 against the urging force of springs 92. At the upper end of gap 93 is an enlarged portion 94 which the peg 58 enters when the locking lever arrangement reaches the position shown in FIG. 10. At this point, further clockwise movement of the lever arrangement 10 is prevented, because the bias of springs 92 causes the peg 58 to become locked in the enlarged portion 94. The arrangement is such that the peg 58 can only be removed from this position by applying upwards hand pressure on the protruding part of rod 81 to overcome the pressure of springs 92.

It has already been mentioned that, as the magazine unit 11 is swung into position, the lever 54 enters the cut-out 56. During the above described clockwise movement of the lever arrangement 79 in order to lock the magazine unit in position, the movable link member 87 also moves downwards towards the lever 54. As will be clear from FIG. 10, the link member 87 is equipped with a blind cut-out portion 95, which tapers towards the top end. As the link member 87 moves downwards, the enlarged end 55 of lever 54 enters the cutout portion 95 and the lever 54 is moved to rotate the transfer plate 51 to a position corresponding to the angular position of cam 73 at that moment. The top of cut-out portion 95 is sized to snugly receive the enlarged end 55 of lever 54 so that, as the movable link members 87, 88 move backwards and forwards along the rods 80, 81 in response to rotation of the cam 73, the lever 54, and hence transfer plate 51 are also moved.

Further two cams 96 and 97 are mounted for rotation on shaft 74, and are arranged to operate respective microswitches 98 and 99. These microswitches are connected in the electric circuit to the drive motor and vacuum pump to control the sequence of operation of the dispenser. Since the connections do not form part of the invention, they will not be described further. A further microswitch, referenced 100, is operated by the button 9 to start the cycle of operation of the dispenser. A similar microswitch (not shown) is used to ensure that the electrical circuit will not operate until the carriage 4 is pushed fully home.

A further safety feature prevents operation of the electrical circuit until the cams 72 and 73 and movable link member 87 are in the correct relative positions, and thus prevents operation of the circuit until the locking lever assembly is moved properly into the locking position shown in FIG. 10. To this end the cam 72 is provided with an electrically conducting pin 101 mounted parallel to shaft 74 in an insulated bushing 102. The pin extends through the cam from one face to the other. A further conducting pin 103 is mounted in an insulating bushing in a frame 104 attached to the housing 1. The pin 103 is threaded at its rear end and is provided with nuts 105 by which electrical connections can be made. Finally a stud 106 is provided on cam follower 90 and is electrically connected to earth.

The electrical circuit is arranged such that its operation is inhibited until the pin 103 is grounded via the pin 101 and stud 106. This required alignment of pins 101, 103 and stud 106 which will only be possible at one particular relative position of cams 72 and 73 and locking lever assembly 79. It should be noted that, once operation has started, alignment of these items is not necessary.

Figure 11:
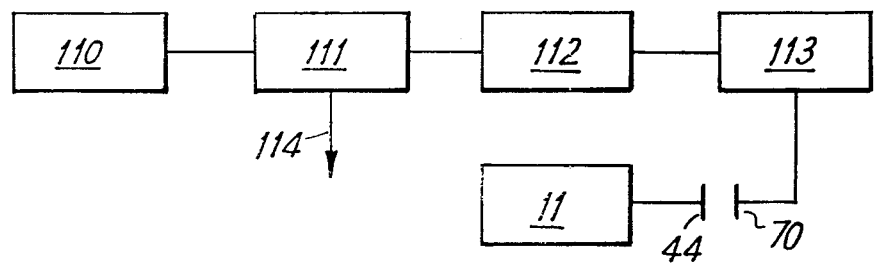
FIG. 11 is a block diagram of the vacuum system used to supply suction to the magazine unit of FIG. 2.

FIG. 11 shows, in block diagram form, the arrangement of the principal parts within the housing 1 which provide the suction to the transfer pipes 31. The pipes 31 are all commoned in the passageway 39 and are connected to a pipe which extends, via orifices 44 and 70, into the interior of housing 1. Within the housing 1 is a vacuum pump 110 connected to a solenoid operated diverter valve 111 having a vent 114 to atmosphere. The output of the valve 111 is connected via a silencer 112 and air filter 113 to the orifice. The valve 111 is such as to connect the orifice 70 either to the pump 110, to provide the necessary suction, or to atmosphere, so that not only is the vacuum released from the passageway 39, but the passageway is vented to atmosphere. A suction pressure of approximately 10" of mercury has been found satisfactory.

The operation of the above described dispenser will now be explained, on the assumption that the magazine unit 11 has been fitted in the recess 2 of the housing as described above. The switch 10 is first operated to switch on the main supply to the dispenser, and this supplies power to the vacuum pump 110. During this period, the valve 111 is operable to vent orifice 70 to atmosphere, so no suction is applied to the transfer pipes 31.

A petri dish containing gel and onto which has been introduced the organism under test is placed on the carriage 4 which is then pushed inwards so that the petri dish lies directly underneath the magazine unit 11. As mentioned previously, the action of pushing the petri dish under the magazine unit depresses the microswitch operating button 9 to thus initiate the cycle of operation of the dispenser. This microswitch switches on an electric motor (not shown) within housing 1 which rotates cams 72, 73, 96 and 97.

Referring now particularly to FIG. 7, the cycle of operation begins with the transfer plate 51 in the fully clockwise position—i.e. with the apertures 27 and 60 in register. As the cycle proceeds, rotation of cam 73 causes the plate 51 to be moved anticlockwise in the direction of the arrow A in FIG. 7 to its extreme anticlockwise position, as shown in FIG. 7. During this movement, the sloping surface 64 pushes the stack 20 of discs upwards against the bias of spring 22 without actually moving the lower disc, which is constrained against leftward movement by the lugs 25 on the cartridge. In the extreme anticlockwise position of plate 51, the shoulder 63 latches behind the bottom disc in the stack. The cycle then proceeds with clockwise motion of plate 51, during which movement the bottom-most disc is slid off the stack 20 and moved to the right to eventually lie in register with the adjacent aperture 30, as shown by reference 120.

The profile of cam 73 is such that the plate 51 remains in the position shown in FIG. 7 for a short period. During this period, the profile of cam 72 is such as to cause the protrusions 41 and 43 to be moved downwards, to thereby cause all of the transfer pipes 31 simultaneously to move downwards towards the gel surface. Also during this period, the cam 96 operates microswitch 98 to switch the diverter valve 111 to connect orifice 44, and hence all of the transfer pipes, to the vacuum pump 110, thus causing a suction to be applied at the bottom ends of each of the transfer pipes. The effect of this suction in combination with the downwards movement of the transfer pipes is to pick up the disc 120 left by movement of plate 51 during the preceding cycle and carry the disc downwards to the gel surface. The disc is held by the suction onto the free end of the respective transfer pipe during this downwards movement. In this way, the discs are transferred onto the gel surface whereupon further movement of the transfer pipes 31 is inhibited, and (as explained above) the transfer pipes slide with respect to the support plate 34, which latter continues its downwards movement for a short distance. The discs are thus pressed downwards onto the surface of the gel by a force approximately equal to the weight of the transfer pipes 31.

At the bottom limit of movement of the support plate 34, the diverter valve 111 is once more switched, by means of the cam 96 and microswitch 98, to vent orifice 44, and hence pipes 31, to atmosphere. The discs are thus released from the ends of the tubes and remain in place on the gel surface.

Finally, the support plate 34, and tubes 31 are raised back to their original position, as shown in FIGS. 4 and 5A before beginning the next cycle. Once the tubes 31 have returned to their original position, the transfer plate 51 is then free to undertake its rightwards movement (as seen in FIG. 7) to transfer the next disc from the bottom of stack 20 to the pick-up position in register with aperture 30.

The cycle of operation is halted by the action of the cam 97 which operates microswitch 99 to switch off the power to the electric motor.

Indicator lamps 121 and 122 on the front panel of housing 1 allow visual monitoring of the operation of the dispenser. Lamp 121 is switched on as soon as the microswitch button 9 is depressed to initiate the cycle of operation and switched off again by the action of cam 97 and microswitch 99 at the end of the cycle. Lamp 121 thus provides an indication that the machine is in operation. Lamp 122 is arranged to be switched on whenever a fault condition occurs: for example if the carriage 4 is not pushed fully home, or if the cams 72 and 73 and locking lever assembly 79 are not in correct alignment. As a further precaution, lamp 122 can be arranged to be illuminated if, for any reason, one or more of the transfer pipes 31 fails to pick up a disc.

It will be seen that the discs are constrained against free movement for the whole of the dispensing process, which results in a very accurate placement of the discs onto the gel surface. In addition, the discs are pressed into the gel surface by a small, but equal force as between individual discs, thus giving highly reliable results of accurate reproducability.

In a modified form of the invention (not shown), means are provided for allowing automatic feeding of petri dishes into the dispenser in conjunction with a conveyor system allowing automatic stacking of the dishes.

I claim:

1. A dispenser for a stack of flat objects to be dispensed, said dispenser comprising:
   an auxiliary housing containing a plurality of holders for objects to be dispensed, each of said holders being capable of holding a stack of objects;
   a moving means for each stack for moving one object from the end of a corresponding stack to a respective pick-up position;
   a plurality of transfer pipes having suction means connected thereto for holding said one object on the end of said respective transfer pipes, one transfer pipe being located adjacent to each of said stack holders;
   a support plate for slidingly supporting said transfer pipes;
   support plate moving means connected to said supporting plate for moving said support plate from said pick-up position to a second releasing position; and
   suction terminating means connected to said suction means for terminating said suction being applied to said pipes for releasing said object when said pipes are moved into said releasing position.

2. A dispenser as claimed in claim 1, wherein said support plate has a plurality of apertures therethrough, said apertures being equiangularly spaced about a circle and said transfer pipes having a collar for supporting said pipes in corresponding apertures for limited longitudinal movement therein.

3. A dispenser as claimed in claim 2, wherein said holders are equiangularly spaced about a circle.

4. A dispenser as claimed in claim 3 further comprising:
   a main housing having drive means therein and connected to said auxiliary housing and control means therein, said auxiliary housing being pivotally connected to said main housing for operating said dispenser.

5. A dispenser as claimed in claim 4 further comprising:
   latch means in said main housing for latching said auxiliary housing in an operating position with respect to said main housing.

6. A dispenser as claimed in claim 5, said latch means comprises:
   a lever having a spring biased latch which is pivotally mounted within said main housing, said main housing further having a slot, said latch means protruding through said slot to the exterior of said main housing; and
   a peg mounted on said auxiliary housing, said peg extending into the interior of said main housing when said auxiliary housing is in operating position for engaging said spring biased latch.

7. A dispenser as claimed in 6, wherein said latch comprises:
   a first block fixedly attached to said lever, and a second block slidably mounted on said lever with a gap between said blocks, and said peg being positioned to pass between said blocks through said gap as said lever is rotated, and latch into said aperture.

8. A dispenser as claimed in claim 7, wherein said transfer plate has an outwardly extending arm which extends into said main housing when said auxiliary housing is in said operating position for being loosely trapped in said gap between said blocks, said second block having a cam follower mounted thereon and a cam associated with said cam follower, said cam being driven by said drive means for rotating said transfer plate.

9. A dispenser for a stack of flat objects to be dispensed, said dispenser comprising:
an auxiliary housing having a plurality of holders for holding objects to be dispensed, each of said holders being capable of holding a stack of objects;
a rotatable transfer plate mounted on said auxiliary housing having on one surface thereof an upstanding ridge coaxial with the axis of rotation of said plate, said ridge being comprised of a series of adjacent teeth, equal in number to the numbers of holders, each respective tooth shaped for moving one object from the end of a respective stack to a respective pick-up position, when said plate is moved from a first angular pick-up position to a second angular releasing position;
transfer pipes supported by said transfer plate and having suction means attached thereto for applying suction for holding said one object on the end of each respective pipe;
pipe moving means connected to said transfer plate for moving said pipes from a first position, where corresponding pipes pick-up said objects by suction, to a second releasing position and for terminating said suction for releasing said object when said pipes are moved to said second releasing position.

10. A dispenser as claimed in claim 9, further comprising a cartridge for containing each stack of objects, and wherein said holders are shaped to receive respective cartridges.

11. A dispenser as claimed in claim 9, further including rotating means connected to said transfer plate for rotating said transfer plate backwards and forwards over an arc smaller than the angular distance between each of said adjacent teeth and each tooth has a shape for allowing it to slide over its respective stack without moving an object therein, when said transfer plate is rotated from said second angular position to said first angular position.

12. A dispenser as claimed in claim 11, wherein said transfer plate has apertures therethrough located between each of said teeth, said apertures being parallel to the axis of said plate, and wherein said pick-up position is the position wherein said object is substantially aligned with a respective one of said apertures when said plate is in said first position.

13. A dispenser as claimed in claim 12, wherein each of said transfer pipes is parallel with the axis of rotation of said transfer plate and aligned with respective apertures of said transfer plate when said plate is in said first position.

14. A dispenser as claimed in claim 13, wherein said pipe moving means further includes simultaneous axial moving means for causing simultaneous axial movement of each of said respective pipes.

15. A dispenser as claimed in claim 14, wherein each of said pipes passes through a respective aperture in said transfer plate, said pipes being supported by said transfer plate when said transfer plate is held stationary in said first position, and subsequently moving said pipes from said first position to said second position.

* * * * *